(12) United States Patent
Soerensen et al.

(10) Patent No.: US 7,661,162 B2
(45) Date of Patent: Feb. 16, 2010

(54) SURGICAL HEAD CLAMP

(75) Inventors: Niels Soerensen, Wuerzburg (DE); Hermann Ziaja, Burgthann (DE); Winfried Kreidler, Tuttlingen (DE)

(73) Assignee: Gottfried Storz Medizintechnik GmbH & Co. KG, Tuttlingen (DE)

( * ) Notice: Subject to any disclaimer, the term of this patent is extended or adjusted under 35 U.S.C. 154(b) by 352 days.

(21) Appl. No.: 11/738,625

(22) Filed: Apr. 23, 2007

(65) Prior Publication Data

US 2007/0250071 A1 Oct. 25, 2007

(30) Foreign Application Priority Data

Apr. 24, 2006 (DE) .................. 20 2006 006 734 U

(51) Int. Cl.
*A61B 19/00* (2006.01)
(52) U.S. Cl. .......................................................... 5/622
(58) Field of Classification Search ...................... 5/622, 5/637, 640, 643
See application file for complete search history.

(56) References Cited

U.S. PATENT DOCUMENTS

| 3,835,861 | A |  | 9/1974 | Kees, Jr. et al. |
| 4,169,478 | A |  | 10/1979 | Hickmann |
| 5,254,079 | A |  | 10/1993 | Agbodoe et al. |
| 5,269,034 | A | * | 12/1993 | Day et al. ......................... 5/637 |
| 5,318,509 | A | * | 6/1994 | Agbodoe ...................... 602/32 |
| 6,381,783 | B2 | * | 5/2002 | Reinhardt et al. ............... 5/622 |

FOREIGN PATENT DOCUMENTS

DE 197 18 535 A1 11/1998

(Continued)

*Primary Examiner*—Frederick Conley
(74) *Attorney, Agent, or Firm*—McGlew and Tuttle, P.C.

(57) ABSTRACT

A surgical head clamp is provided including an essentially U-shaped retaining clip (1) with two holder arms (3, 4), running towards the same side in the plane thereof at the ends of a connecting bar (2). The arm ends (5, 6) of the holder arms have mandrel holders (11) mounted adjustably in bearings that are coaxial to one another. The mandrel holders may be provided with one or more said holding mandrels (12), whereby a first mandrel holder is pivotably fastened at a bearing part (15) of the one arm end (6), which bearing part is adjustable around a common bearing shaft (9), and a second mandrel holder (11) can be adjusted by means of a threaded spindle (10) in a bearing bore (7) of the other said arm end (5). The second mandrel holder (11) includes a guide shank (50) that is provided with a socket bore (54) on the front side, which is mounted coaxially to the bearing shaft (9) in a spring-mounted manner in a axial bore (61) of the threaded spindle (10). The threaded spindle (10) is provided with an external thread and is adjustably mounted in a smooth cylindrical bearing bore (7) of the other arm end (3). The external thread is embodied as a ball thread (23), which has an arcuate-segment profile, with which two balls (24, 25) mesh as contact elements. The balls are arranged in a diametrically opposed, axially fixed manner in the wall (28) of the bearing bore (7) and are held in contact with the ball thread (23) by an adjustable locking lever (35) in the locked position thereof, and which can be brought out of contact with the threaded spindle (10) in another position in order to make the threaded spindle (10) freely displaceable in its said bearing bore (7).

12 Claims, 4 Drawing Sheets

FOREIGN PATENT DOCUMENTS

| | | |
|---|---|---|
| DE | 694 11 621 T2 | 3/1999 |
| DE | 198 41 250 | 2/2000 |
| DE | 199 55 374 A1 | 5/2001 |
| DE | 202004006726 U | 7/2004 |
| EP | 0 623 318 B1 | 11/1994 |

* cited by examiner

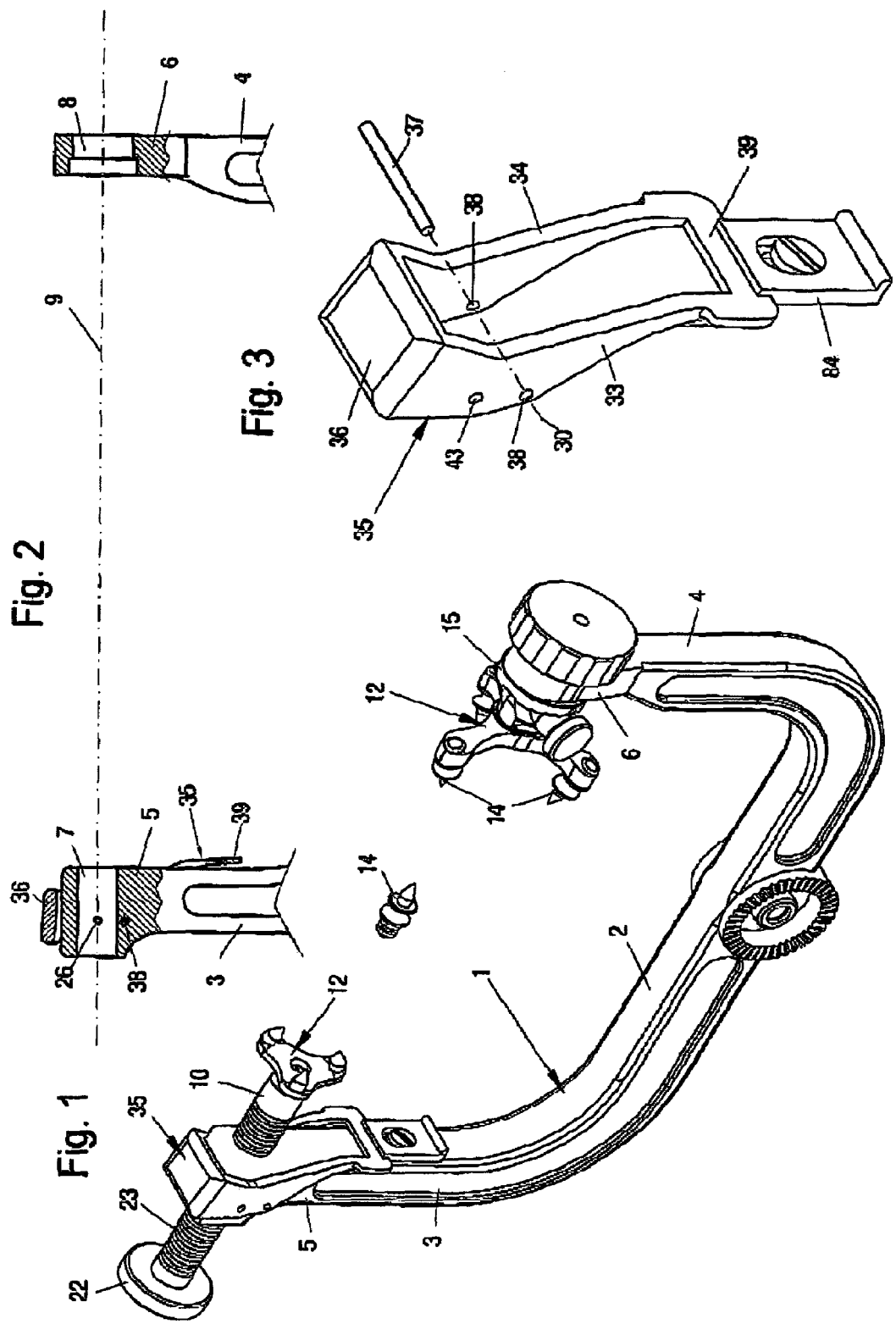

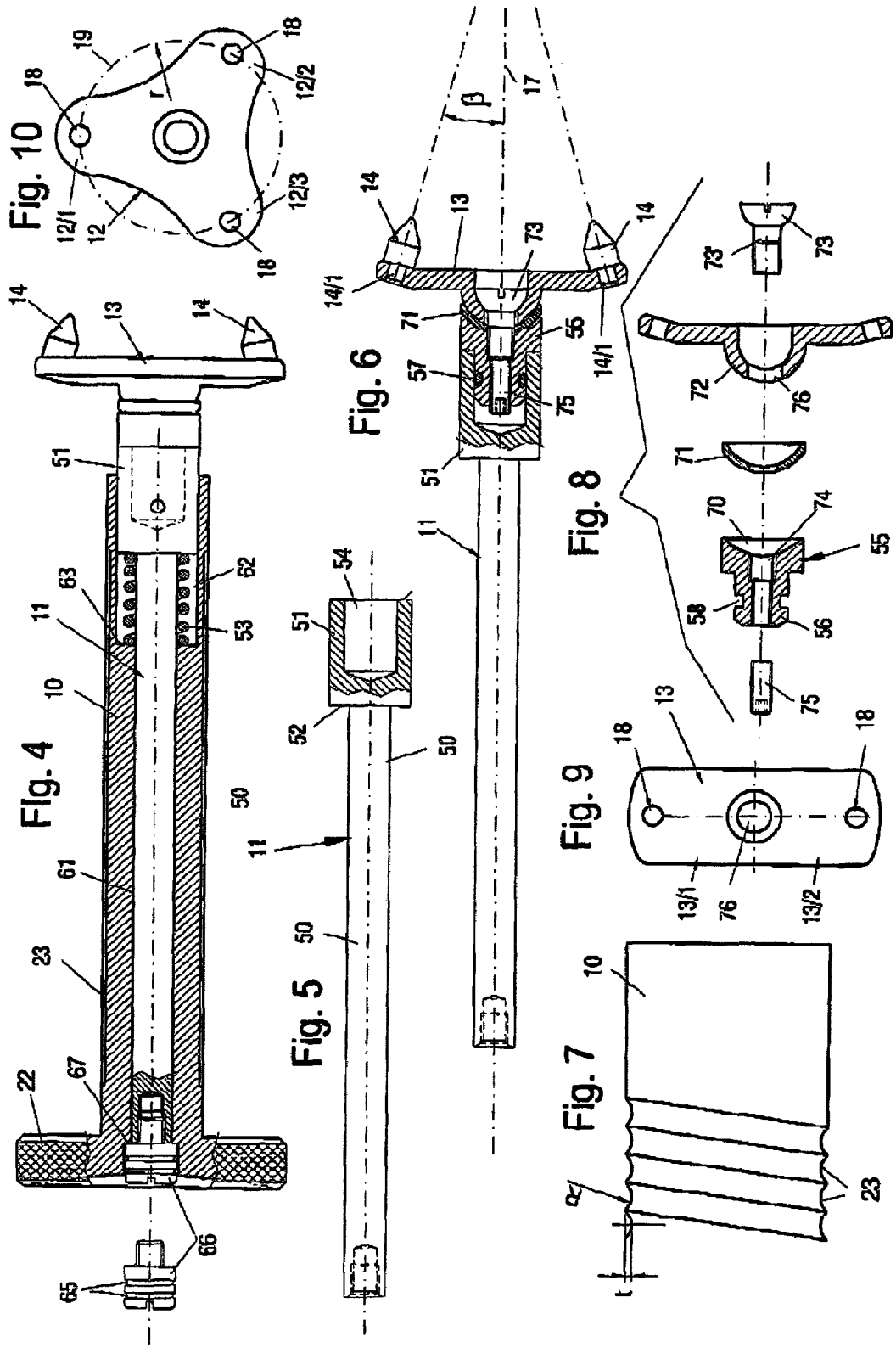

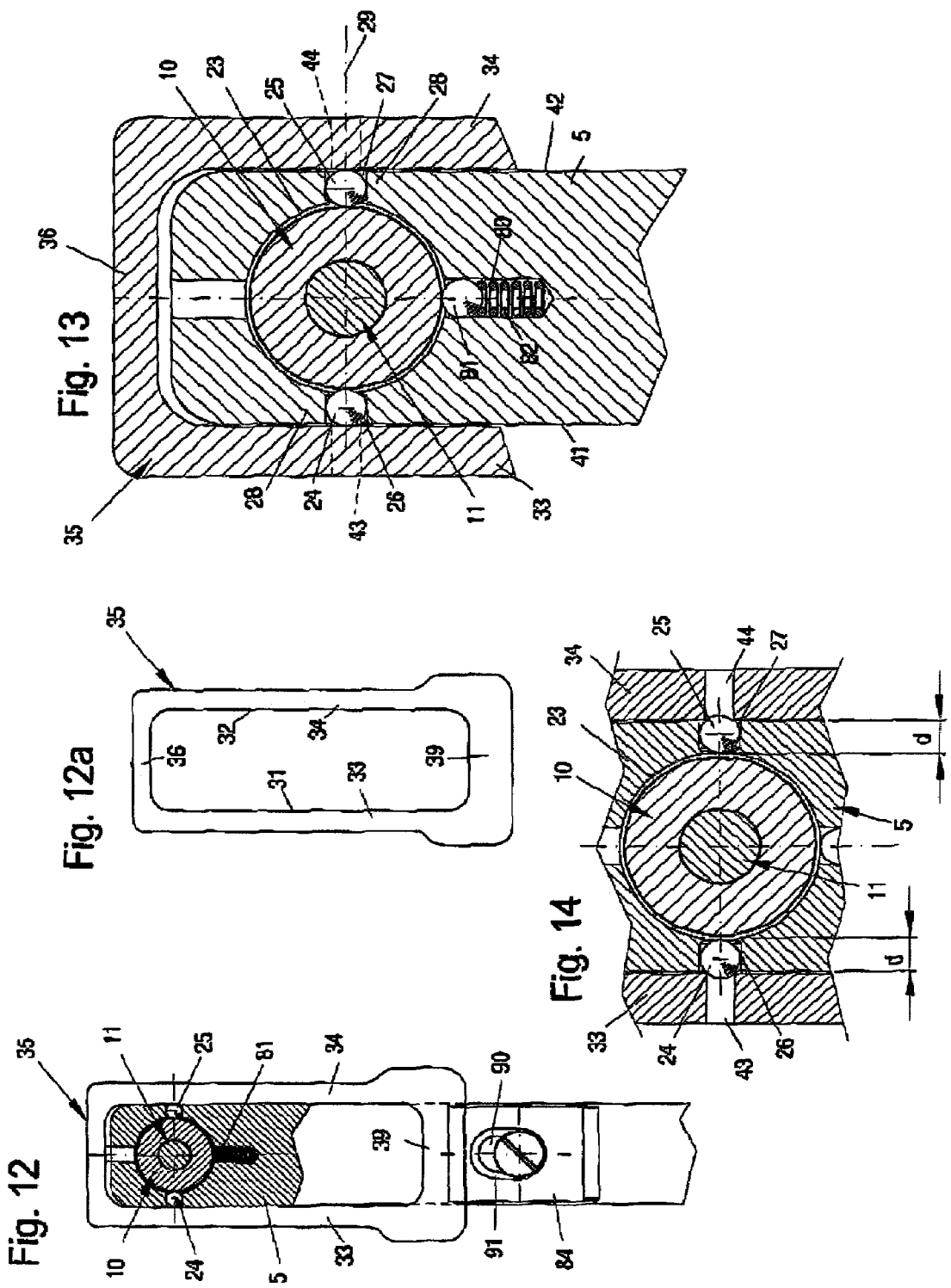

SURGICAL HEAD CLAMP

CROSS REFERENCE TO RELATED APPLICATIONS

This application claims the benefit of priority under 35 U.S.C. § 119 of German Patent Application DE 20 2006 006 734.5 filed Apr. 24, 2006, the entire contents of which are incorporated herein by reference.

FIELD OF THE INVENTION

The present invention pertains to a surgical head clamp consisting of an essentially U-shaped retaining clip with two holder arms running towards the same side in the plane thereof at the ends of a connecting bar, the arm ends of which holder arms have mandrel holders mounted adjustably in bearings that are coaxial to one another, which mandrel holders may be provided with one or more holding mandrels, whereby a first mandrel holder is pivotably fastened at a bearing part of the one arm end, which bearing part is adjustable around a common bearing shaft, and a second mandrel holder can be adjusted by means of a threaded spindle in the bearing bore of the other arm end.

BACKGROUND OF THE INVENTION

A head or skull clamp of this type, in which the one holder arm has a two-arm mandrel holder, which is rotatable in an axial bore of the holder arm by means of a special bearing device and can be fixed in different rotated positions, has already become known from DE 694 11 621 T2 (=EP 0 623 318 B1). The two-arm mandrel holder is mounted in a fork-shaped holding device to pivot about a pivot axis running transversely to the bearing shaft.

A single mandrel opposing the two-arm mandrel holder is mounted in a threaded spindle, which is inserted in the opposite holder arm coaxially to the bearing shaft of the two-arm mandrel holder. The threaded spindle can be adjusted axially by rotating by means of a rotary knob designed as a knurled disk, such that the distance of this single mandrel from the two mandrels of the two-arm mandrel holder is variable and can be adjusted to the patient's head to be fixed in each case. The single mandrel can be mounted in a spring-mounted manner in the threaded spindle in the axial direction.

In this prior-art head clamp, the connecting bar connecting the two holder arms, lying in a common plane, has a two-part design and can be lengthened or shortened in its direction of extension, such that a coarse change in distance is possible between the single mandrel and the two mandrels of the two-arm mandrel holder.

A bracket provided with a toothed ring, by means of which the entire head clamp can be fastened at a frame in various pivoting positions, is provided at one part of the connecting bar. In this case, the axis of the toothed ring, about which the entire head clamp can be pivoted and fixed in the one or other pivoting direction, runs at right angles to the common bearing shaft of the threaded spindle and of the bearing of the two-arm mandrel holder.

However, it has arisen in practice that two-arm mandrel holders on the top side opposite the single mandrel are not optimal for all applications, and that the two-part design of the connecting bar, by means of which the coarse distance adjustment can be made, brings with it an awkward handling as well, which requires improvement.

Other head clamps have also become known from U.S. Pat. Nos. 3,835,861, 4,169,478 and 5,254,079. In these as well, only one two-arm mandrel holder is provided on the side opposite the single mandrel, respectively. The connecting bar has a two-part design for the coarse distance adjustment. In this case, a part of the connecting bar is provided with saw-tooth-like locking teeth, with which a locking member provided with locking teeth, meshes in a spring-mounted, detachably locking manner.

In all these head clamps, the mandrel holder of the single mandrel is mounted in the cylindrical cavity of a threaded spindle in the form of a piston that is displaceable against spring pressure and is provided on the front side with a socket bore for receiving the single mandrel. On the front side facing away from the single mandrel, a stop screw is screwed into the holder shank, whose head with a supporting disk lies against the front surface of a knurled gripping part. Thus, an axial quick adjustment with abolishing of the threaded contact is not possible.

Head clamps, in which the hollow spindles, into which the mandrel holders are axially displaceably mounted against spring pressure by means of threaded contacts, have external locking teeth, with which detachable locking elements mesh in a fixed manner, have become known from DE 197 18 535 C2 and DE 20 2004 006 726 U1. By loosening the locking elements, the hollow spindles are freely displaceable in their bearing bores.

SUMMARY OF THE INVENTION

The basic object of the present invention is to create a surgical head clamp of the type mentioned in the introduction, which, with a simpler construction, makes possible an easier handling, in particular a simpler adjustment and fixing of the adjustable mandrel holder and with gentle action, a better fixing of a patient's head, whereby the threaded spindle shall be freely displaceable in the holder arm with abolishing of the threaded contact.

This object is accomplished according to the present invention in that the second mandrel holder comprises a guide shank provided with a socket bore on the front side, which is mounted in the threaded spindle in a spring-mounted manner coaxially to the bearing shaft, and in that the threaded spindle, which is provided with an external thread, is adjustably mounted in a smooth cylindrical bearing bore of the other arm end, whereby the external thread is embodied as a ball thread with a circle-segment-like profile, with which two balls, as contact elements, mesh, which are arranged in the wall of the bearing bore in a diametrically opposed, axially fixed manner and which are held in contact with the ball thread by means of an adjustable locking lever in its locked position and which can be brought out of contact with the threaded spindle in a different position of the locking lever in order to make the threaded spindle freely displaceable in its bearing bore.

With the embodiment according to the present invention, it is possible to simply use a two-arm or three-arm mandrel holder depending on the respective needs on both clamping sides and thus to achieve the respective optimal clamping of the patient's head to be treated. Moreover, the coarse distance adjustment between the single mandrel and the respective, opposite mandrel holder, which is provided with a plurality of mandrels, can be made in a considerably simpler, more comfortable and above all clearer manner, such that the handling is overall simpler and more reliable than with the prior-art head clamps, in which the two clamp arms can be adjusted against one another.

In the prior-art head clamps, in which the hollow threaded spindle detachably meshes with an internal thread of the bearing bore of the clamp arm, a free displacement of the threaded spindle is not possible. The threaded spindle may only be adjusted axially by means of rotary movements, like a screw.

On the other hand, in the design of the threaded contact according to the present invention, it is possible to abolish the threaded contact and to randomly position the threaded spindle together with the mandrel holder in the axial direction selectively in stroke lengths, which correspond in each case to the single or multiple pitch of the ball thread. With locked meshing of the balls a fine adjustment can be made by rotating the threaded spindle. A threaded contact between the mandrel holder and the threaded spindle can be eliminated.

By features of an embodiment according to the invention it is guaranteed that after each manual coarse adjustment, the threaded spindle inevitably assumes an axial position, in which the two balls immediately find a correct meshing position, so that thread damage during the changing over of the locking lever into its locked position can be avoided with certainty.

Further advantageous embodiments of the present invention make possible a securing of the locking lever in its locked position in a simple manner and with simple means.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a lateral perspective view of a head clamp according to the invention;

FIG. 2 is a sectional view of the two holder arm ends with their bearing bores;

FIG. 3 is an enlarged perspective view of the locking lever from FIG. 1 as a single part with locking slide;

FIG. 4 is a sectional view of a threaded spindle with a mandrel holder;

FIG. 5 is a partially sectional view showing the mandrel holder from FIG. 4 as a single part;

FIG. 6 is a sectional view of the mandrel holder from FIG. 5 with a mandrel carrier;

FIG. 7 is an enlarged view of the end section of the threaded spindle from FIG. 4;

FIG. 8 is an exploded view of the sectional view of a two-arm mandrel carrier with its fastening parts;

FIG. 9 is a front view of the two-arm mandrel carrier;

FIG. 10 is a front view of the three-arm mandrel carrier;

FIG. 12 is a partly cutaway, front view XII from FIG. 11;

FIG. 12a is a front view of the locking lever from FIG. 12 as a single part;

FIG. 13 is a sectional view of an enlarged cutout from FIG. 12; and

FIG. 14 is a sectional view cutout from FIG. 13 with another functional position of the locking lever and the threaded balls.

DESCRIPTION OF THE PREFERRED EMBODIMENTS

Figure 11:
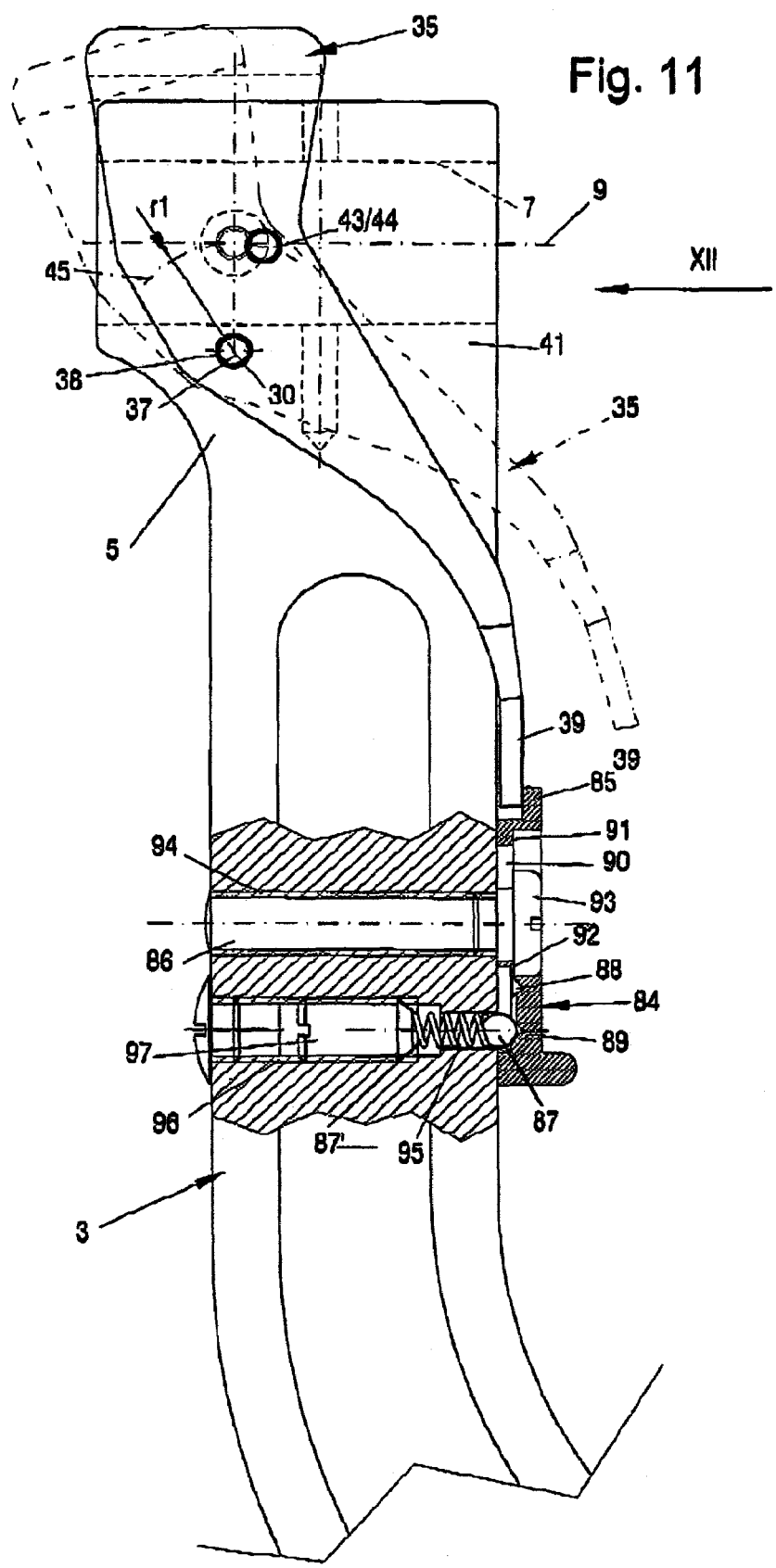
FIG. 11 is a somewhat enlarged, lateral view of a clamp arm with the locking lever and a sectional view of its securing means.

Referring to the drawings in particular, the head clamp shown in the drawing figures comprises a U-shaped retaining clip 1, which has holder arms 3 and 4 running towards the same side at the ends of a single-part connecting bar 2 in the plane thereof.

The upper ends 5 and 6 of the holder arms 3 and 4 are each provided with bearing bores 7 and 8, respectively, that are coaxial to one another, which have a common bearing shaft 9 (see FIG. 2). The bearing bore 7 is used for mounting and guiding a threaded spindle 10, in which is mounted a mandrel holder 11 (FIGS. 4 through 6). This mandrel holder 11 is provided with a three-arm mandrel carrier 12 in the embodiment shown in FIG. 1. However, as described in further detail below, it may be provided either with a two-arm mandrel carrier 13 or with a single holding mandrel 14 that is coaxial to the bearing shaft 9.

The opposite bearing bore 8 of the other holder arm 4 is used for mounting a bearing part 15, at which either a three-arm mandrel carrier 12 or a two-arm mandrel carrier 13 can likewise be fastened.

The bearing part 15 can be pivoted about the bearing shaft 9 in the bearing bore 8 by means of a special bearing device and can be fixed in different angular positions.

While the two-arm mandrel carrier 13 has two, symmetrical and diametrically opposed arms 13/1 and 13/2 with respective, inwardly sloped ends, the three-arm mandrel holder 12, as is obvious from FIG. 10, has three arms 12/1, 12/2 and 12/3, which have the same angular distances of 120° each from one another and the socket bores of which 18 lie on a concentric circle 19 with the radius r. The external sections, arms 12/1, 12/2 and 12/3, are likewise sloped uniformly towards the central middle shaft.

Since the axes of the holding mandrels 14 coincide with the axes of their socket bores 18, the axes of the holding mandrels 14 also intersect at the same point on the middle shaft, which coincides with the bearing shaft 9 in a normal position of the three-arm mandrel holder 12.

The holding mandrels 14, which establish the connection for the patient's head to be secured, are, as usual, provided with a socket pin 14/1 fitting in a socket bore 18 (FIG. 6).

The holding mandrels 14 of the two-arm mandrel carrier 13 are also symmetrically sloped towards its middle shaft, so that its axes 16 form an acute angle with this middle shaft 7 (FIG. 6).

The mandrel holder 11 consists of a cylindrical guide shank 50 and a head part 51 with an enlarged diameter, which head part 51 forms a stop shoulder 52 for a compression spring 53. The head part 51 has a socket bore 54 open on the front side, which is used for the frictionally engaged mounting of the cotter pin 55, at which either a two-arm or three-arm mandrel carrier 13 or 12, respectively, can be fastened.

The cotter pin 55 is provided with a socket pin 56 with reduced diameter, which has an elastic O-ring 57, which is preferably made of rubber or plastic, for increasing the frictional engagement in a ring groove 58.

The outwardly directed front surface of the cotter pin 55 is provided with a dome-shaped recess 70. With the interposition of a likewise dome-shaped plastic disk provided with holes, a hemispherical, dome-shaped wall 72 of a mandrel carrier 13 or 12 is pivotably and rotatably mounted in the recess 70 and is connected to the cotter pin 55 by means of a ball end screw 73. As shown in FIG. 6, the ball end screw 73 is screwed into a central threaded bore 74 of the cotter pin 55 and is fixed in an axial position by means of a counterscrew 75, such that the mandrel carrier 12 or 13 is held in its respective pivoted position in a frictionally engaged manner, but can be easily pivoted and rotated manually or when putting on a patient's head. In order to guarantee a sufficiently large pivotability of the mandrel carrier 12, 13, the dome-shaped wall 72 is provided with a central bore 76, whose diameter is greater than the threaded shaft 73' of the ball end screw 73.

As is obvious from FIG. 4, the threaded spindle 10 has a central axial bore 61, in which the guide shank 50 of the mandrel holder 11 is guided in an axially movable manner. For the axial movable mounting and guiding of the head part 51, which has a larger diameter, an expanded, coaxial mounting bore 62 is provided, which forms a ring shoulder 63 with the axial bore 61. Between this ring shoulder 63 and the stop shoulder 52 of the head part 51 is located the compression spring 53 enclosing a part of the guide shank 50, which permits a certain spring stroke when clamping a patient's head. How intensely the compression spring 53 is loaded can be read at the peripheral grooves 65 of a slotted headless screw 66, which is screwed into the guide shank 50 on the front side and at the same time is used as a movement limiting means, when it lies against a rear ring shoulder 67 of the axial bore 61.

To be able to clamp a patient's head firmly between the mandrel carrier 12 or 13 fastened in the mandrel holder 11 and the holding mandrels 14 of the opposite three-arm mandrel carrier 12, the mandrel holder 11 has to be adjustable in the bearing shaft 9. For this purpose, not only is the mandrel holder 11 mounted in an axially spring-mounted manner in the threaded spindle 10, but also the threaded spindle 10 provided with the knurled handle 22 is provided on the outside with a ball thread 23 and is mounted axially adjustably in the bearing bore 7 of the holder arm 3. This bearing bore 7 has a smooth, cylindrical internal surface, so that the ball thread is not in contact with the bearing bore 7, but rather is freely displaceable therein.

However, as contact elements, two identical balls 24, 25 are in contact with the ball thread 23, which balls 24, 25 are mounted in a radially movable manner, but in a fixed manner in the axial direction of the bearing shaft 9 in two radial bores 26 and 27 which are diametrically opposite at the level of the bearing shaft 9. These radial bores 26, 27 have a common axis 29, and they are located in the bore wall 28 surrounding the bearing bore 7. In the area of these radial bores 26, 27, this bore wall 28 has a thickness d (FIG. 14), which is smaller than the diameter of the balls 24, 25. In the exemplary embodiment, the balls 24, 25 have a diameter of 3 mm, while the wall thickness d is 2.7 mm.

It is understood that the profile of the ball thread 23 is consistent with the ball diameter, such that the threaded spindle 10 can be rotated easily and be displaced in the bearing bore 7 in a controlled manner depending on the direction of rotation, when the balls 24, 25 are in contact with it.

The profile radius R of the ball threads 23, which have a circle-segment-shaped profile, is 1.5 mm and thus corresponds to half the ball diameter. The balls 24, 25 are held in contact with the ball thread 23 by means of two plane-parallel internal surfaces 31, 32 of the fork-shaped arms 33, 34 of a locking lever 35.

On its upper end section in whose area the two radial bores 26, 27 also lie, the holder arm 3 has two, flat, external limiting surfaces 40, 41, which run at right angles to the common axis 29 of these two radial bores 26, 27, against which the fork-shaped arms 33, 34 with their likewise planar internal surfaces 31, 32 lie free from backlash. The radial bores 26, 27 can be covered by means of these internal surfaces 31, 32 in the planes of the limiting surfaces 40 and 41, respectively. The locking lever 35 is mounted at the holder arm 5 to pivot about a pivot axis 30 (FIGS. 3 and 11) parallel to the axis 29 of the radial bores 26, 27. A bearing pin 37, which is fastened in the holder arm 3 and protrudes into bearing bores 38 of the two fork-shaped arms 33 and 34, is used as a bearing element. The two fork-shaped arms 33 and 34 are rigidly connected to one another on the top side by means of a plate-like, horizontal crossbar 36 and at its lower ends by means of a vertical crossbar 39, such that they can be actuated together.

The end sections of the fork-shaped arms 33, 34, which are extended downwards and are connected to one another by means of the crossbar 39, together form a handle, with which the locking lever 35 can be easily actuated.

When the two plane-parallel internal surfaces 31 and 32 of the fork-shaped arms 33, 34 of the locking lever 35 cover the radial bores 26, 27, the two balls 24, 25 used as contact elements cannot shift radially outwardly. They are then in positive forced contact with the ball thread 23, and thus fix the threaded spindle 10 in the bearing bore 7. In this locked position of the locking lever 35 and of the balls 24, 25, the threaded spindle 53 can be moved more or less slowly in the axial direction not freely, but only by means of rotating.

To enable the balls 24, 25 to shift in the radial direction within the radial bores 26, 27 and to make possible a free, axial, adjusting movement of the threaded spindle 10, the two fork-shaped arms 33 and 34 of the locking lever 35 have bores 43 and 44, which lie on an arc 45 that is concentric to its pivot axis 30 and are aligned with one another. These bores 43, 44 have a smaller diameter than the balls 24, 25 and are designed, such that the balls 24, 25 are able to penetrate in them radially to the extent that they are able to come out of contact with the ball thread 23 of the threaded spindle 10. I.e., the balls 24, 25 may partly dip into the bores 43, 44 for the release of the threaded spindle 10. The radius r1 of the arc 45 (FIG. 11) corresponds exactly to the distance of the bores 43, 44 from the pivot axis 30 of the locking lever 35. In [the] exemplary embodiment, the balls 23, 24 have a diameter of 3 mm and the bores 43, 44 have a diameter of 1.8 mm.

As is obvious from FIGS. 12 and 13, a locking ball 81, which is the same size as the balls 23, 24, is located in the bearing bore 7 in a vertically and radially running blind bore. This locking ball 81 is held in contact with the ball thread 23 of the threaded spindle 10 in a spring-mounted manner under the influence of a compression spring 82. Compared to the balls 24, 25, this locking ball is offset by 90° in the circumferential direction and by one-fourth of the thread pitch in the axial direction of the bearing shaft 9. It is thus guaranteed that, after each free lengthwise displacement, the threaded spindle 10 immediately assumes an axial position, in which the two balls 24, 25 are able to achieve contact correctly with their ball thread and the locking lever 35 is likewise able to immediately be brought into its locked position. Consequently, the risk of mechanical damage to the ball threads 23 is avoided.

To be able to prevent the locking lever 35 from being able to unintentionally pivot out of its locked position shown in solid lines in FIG. 11, in which it holds the two balls 24, 25 in contact with the ball thread 23 and to abolish the lock, the locking lever 35 can be locked in its locked position covering the radial bores 26, 27. For this purpose, a locking slide 84, which, in its locked position shown in FIG. 11, fixes the lower crossbar 39 of the locking lever 35 with a locking tongue 85, is arranged on the inside of the holder arm 3. This locking tongue is vertically displaceably mounted at the holder arm 3 by means of a screw 86 and can be locked, on the one hand, in the locked position shown, and, on the other hand, in a downwardly offset, inactive position by means of a spring-mounted locking ball 87. For this purpose, the locking slide 84 is provided with two locking notches 88 and 89, with which the locking ball 87 can mesh in a selectively locking manner.

For receiving the threaded shank of the screw 86, the locking slide 84 is provided with a vertical slot 90, on whose sunk edge 91 the planar ring surface 92 of the screw head 93 sits in a guided manner.

The screw 86 is screwed into a horizontal threaded bore 94 of the clamp arm 3. The locking ball 87 lies together with its compression spring 87' in a bore 95 parallel thereto, to which a threaded bore 96 is connected. In this threaded bore 96 is located an adjusting screw 97, against which is supported the compression spring 87' of the locking ball 87.

To release the locking lever 35, the locking slide 84 is displaced in the downward direction until the locking ball 87 engages the upper locking notch 88. The lower crossbar 39 of the locking lever 35 is then free and the locking lever 35 can be pivoted into the position shown in phantom lines in FIG. 11, in which the two bores 43 and 44 align with the balls 24, 25. Consequently, the forced contact with the ball thread is abolished and the threaded spindle 10 is freely displaceable in the bearing bore 7 or with an overwinding of the locking action of the locking ball 81. In this way, an axial coarse adjustment of the threaded spindle 10 can be made with the mandrel holder 11. After such a coarse adjustment, the locking lever 35 is again brought into its locked position and is locked with the locking slide. The balls 24, 25 are then again located in forced contact with the ball thread 23. The threaded spindle 10 can then be brought exactly into the correct clamping position by means of rotating.

While specific embodiments of the invention have been shown and described in detail to illustrate the application of the principles of the invention, it will be understood that the invention may be embodied otherwise without departing from such principles.

What is claimed is:

1. A surgical head clamp comprising:
    an essentially U-shaped retaining clip with a connecting bar and a first holder arm and a second holder arm extending in a same direction in a plane of said U-shaped retaining clip at ends of said connecting bar, said first holder arm having a first arm end with a first bearing bore and said second holder arm having a second arm end with a second bearing bore having an inner wall with a smooth cylindrical surface and with two balls arranged in a diametrically opposed, axially fixed manner in said inner wall, said first bearing bore being coaxial to said second bearing bore;
    a first mandrel holders mounted adjustably in said first bearing bore and pivotably fastened at a first bearing part of said first arm end, said first bearing part being adjustable around a common bearing shaft;
    a second mandrel holder mounted adjustably in said second bearing bore, said second mandrel holder including a threaded spindle provided with an external thread for adjustment and an axial bore and said second mandrel holder including a guide shank provided with a socket bore on a front side, said guide shank being mounted coaxially to said common bearing shaft in a spring-mounted manner in said axial bore of said threaded spindle, said threaded spindle being adjustably mounted in said second bearing bore of said second arm end, said external thread comprising a ball thread with an arcuate-segment profile, said two balls meshing as contact elements with said arcuate-segment profile;
    an adjustable locking lever connected to said U-shaped retaining clip and having a locked position, said balls being held in contact with said ball thread by means of said adjustable locking lever in the locked position thereof, and said balls being brought out of contact with said threaded spindle in another position of said locking lever in order to make said threaded spindle freely displaceable in said second bearing bore.

2. A surgical head clamp in accordance with claim 1, wherein said U-shaped retaining clip further comprises a locking ball extending in a radially spring-mounted manner from said second bearing bore for meshing with said ball thread.

3. A surgical head clamp in accordance with claim 1, wherein said balls are each mounted in one of plural radial bores, which are coaxial to one another, of wall sections of said inner wall that fittingly receives said threaded spindle, whereby a dimension of openings of said wall sections are each smaller than the ball diameters.

4. A surgical head clamp in accordance with claim 3, wherein said second holder arm has two plane-parallel and flat outer surfaces, running at right angles to a second holder arm axis, at least in the area of said radial bores, at which outer surfaces said locking lever as a two-arm locking lever, is pivotably arranged, said two-arm locking lever having fork-shaped arms and said radial bores each being covered in a plane of one of boundary surfaces of said second holder arm.

5. A surgical head clamp in accordance with claim 4, wherein said locking lever two said fork-shaped arms each have a plane-parallel inner surface lying on outer surfaces of said second holder arm and which are mounted to pivot at said second holder arm about an eccentric pivot axis, which is parallel to said axis of said radial bores.

6. A surgical head clamp in accordance with claim 5, wherein said locking lever fork-shaped arms are connected to one another by means of a crossbar lying above said holder arm, said locking lever having a gripping part, which can be fixed in the locked position of said locking lever by means of a securing means.

7. A surgical head clamp in accordance with claim 6, wherein said gripping part is embodied as another crossbar connecting the ends of said fork-shaped arms, in whose path of movement a locking slide of the securing means is introduced in a locking manner.

8. A surgical head clamp in accordance with claim 4, wherein said two fork-shaped arms of said locking lever have recesses aligned with one another and which lie on an arc that is concentric to a pivot axis, said balls partly going into recesses for the release of said threaded spindle.

9. A surgical head clamp in accordance with claim 8, wherein the recesses consist of said bores having a diameter that is smaller than a diameter of said balls.

10. A surgical head clamp in accordance with claim 1, wherein said socket bore is located in a head part of said guide shank forming a radial ring shoulder for a compression spring, opposite which stands axially a radial ring shoulder of an axial bore of said threaded spindle, said guide shank being provided, on an end opposing the mounting bore, with a stop element limiting its spring-mounted axial movement.

11. A surgical head clamp in accordance with claim 1, further comprising:
    a multi-arm mandrel carrier provided with a plurality of said holding mandrels at said guide shank;
    a cotter pin provided with a plug-in projection fitting into said socket bore, said socket bore having on a front side, a dome-like depression for a pivotable and rotatable mounting of said multi-arm mandrel carrier provided with a fitting counterprofile.

12. A surgical head clamp in accordance with claim 11, wherein for the pivotable fastening of said multi-arm mandrel carrier, a ball end screw fitting a counterprofile is screwed into a central threaded bore of said cotter pin and is fixed by means of a counterscrew.

\* \* \* \* \*